US006640976B1

(12) United States Patent
Franks-Farah et al.

(10) Patent No.: US 6,640,976 B1
(45) Date of Patent: Nov. 4, 2003

(54) MALE CLEAN INTERMITTENT CATHETER SYSTEM

(75) Inventors: Judith Franks-Farah, Northbrook, IL (US); Shirley P. Grey, Wauconda, IL (US); Sylvia D. Aruffo, Highland Park, IL (US); Carol A. Outland, Olympia Fields, IL (US)

(73) Assignee: CareGuide, Inc., Gurnee, IL (US)

( * ) Notice: Subject to any disclaimer, the term of this patent is extended or adjusted under 35 U.S.C. 154(b) by 220 days.

(21) Appl. No.: 09/879,321

(22) Filed: Jun. 12, 2001

Related U.S. Application Data

(60) Provisional application No. 60/211,152, filed on Jun. 13, 2000.

(51) Int. Cl.[7] .............................................. B65D 69/00
(52) U.S. Cl. ........................ 206/571; 206/232; 206/440
(58) Field of Search ...................... 206/232, 570–572, 206/581, 438, 440, 459.5, 364; 604/327–331, 544

(56) References Cited

U.S. PATENT DOCUMENTS

| | | | |
|---|---|---|---|
| 4,080,970 A | | 3/1978 | Miller |
| 4,169,550 A | | 10/1979 | Williams |
| 4,212,392 A | | 7/1980 | McKenzie |
| 4,522,302 A | * | 6/1985 | Paikoff ........................ 206/570 |
| 4,917,238 A | * | 4/1990 | Schumacher ................ 206/223 |
| 5,117,981 A | | 6/1992 | Crawford et al. |
| 5,544,753 A | | 8/1996 | Monica |
| D380,234 S | | 6/1997 | Hipple et al. |
| 5,643,233 A | | 7/1997 | Turner |
| 5,660,176 A | | 8/1997 | Iliff |
| 5,718,245 A | * | 2/1998 | Horn .......................... 206/570 |
| 5,752,234 A | | 5/1998 | Withers |
| 5,785,650 A | | 7/1998 | Akasaka et al. |
| D398,772 S | | 9/1998 | Benham |
| 5,803,249 A | | 9/1998 | Harsanyi, Jr. et al. |
| 5,848,700 A | | 12/1998 | Horn |
| 5,931,304 A | | 8/1999 | Hammond |
| 5,961,446 A | | 10/1999 | Beller et al. |
| 5,979,658 A | * | 11/1999 | Allen et al. ................. 206/572 |
| 6,068,121 A | * | 5/2000 | McGlinch .................... 206/571 |
| 6,090,075 A | * | 7/2000 | House ......................... 604/544 |
| 6,116,426 A | * | 9/2000 | Slonim ........................ 206/570 |
| 6,238,383 B1 | * | 5/2001 | Karram et al. .............. 604/544 |

* cited by examiner

*Primary Examiner*—Luan K. Bui
(74) *Attorney, Agent, or Firm*—Bell, Boyd & Lloyd LLC

(57) ABSTRACT

A method and system for performing intermittent male catheterization by a patient, a patient's caregiver, or a health care provider are revealed. The system contains apparatus for at least one intermittent male catheterization and includes at least one male catheter, antibacterial soap, a lubricant, step-by step-instructions, and a container, where the above named items are positioned inside the container. The method includes self-care documentation for a medical professional to instruct a user in the use of the system and to keep a record that the instruction of the patient was performed.

6 Claims, 8 Drawing Sheets

FIG. 2A

Clean Intermittent Catheterization     Step-by-Step    page 1

*This guide is to be followed only on the order of a physician. This guide is not a substitute for your health care professional's instructions. All the medical supplies you need are in this kit. The name of each item is printed in color below. Read all the steps and use the Map to locate each one before you begin. Keep everything in the box until the guide tells you to use it.*

Prepare for Care

1 Get a clean, fresh towel. Wash your hands with Antibacterial Soap and warm water. Dry them only on the fresh towel.

*If you have a caregiver do this for you, they should wash hands and put on the Gloves.*

Spread out two clean paper towels for a work surface. If you are going to do the procedure on a bed or chair, put the Underpad under your buttocks.

2 Wash your penis with the Paper Wash Cloth and Antibacterial Soap and warm water. Clean the head of your penis well, pulling the foreskin back if necessary.

Rinse the Paper Wash Cloth clean, squeeze it dry and place it on a corner of one of the paper towels. Wash and dry your hands again.

*A caregiver wearing gloves does not need to wash again.*

The Catheter

3 Take the Catheter out of the package and lay it on the paper towel. Flip open the cap of the Lubricating Jelly. Squeeze 3 inches of Jelly onto the Catheter, starting at the tip. Be careful not to touch the Catheter with the tube.

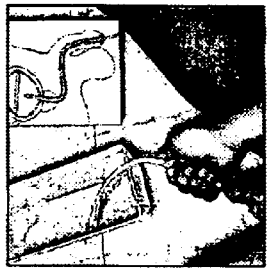

4 Hold the Catheter an inch behind the Jelly. Roll it so that the Jelly covers all sides.

5 Lift the Catheter away from the paper towel and lay the wide end in the Collection Container. Move the Container close to your body so you do not accidentally pull the wide end of the Catheter out.

6 Hold the penis straight out with one hand and insert the Catheter with the other hand. Pull the penis away from your body to keep the channel straight. Push the Catheter in until a bit of urine comes out.

*If the Catheter stops, wait a minute to let the muscles relax, then gently begin to push again.*

7 Slowly push the Catheter in one more inch. Now lower the angle of the penis. The bladder will empty while you hold the Catheter in place. When the urine stops, slowly pull the Catheter out.

*Continued on the back of this page...*

34

Clean Intermittent Catheterization *continued...* page 2

Clean for Next Time

8 Take the Catheter to a sink and wash it with Antibacterial Soap and warm water. Hold the Catheter under running tap water to rinse well, inside and out. Shake it several times to get off extra water.

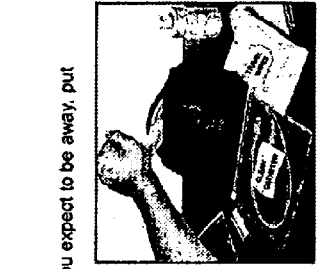

9 Place the Catheter on the clean paper towel to air dry. Pick up the Paper Wash Cloth you left on the paper towel and use it to remove any Jelly left on the head of your penis. Pull the foreskin back down.

10 Check the level of urine in the Container. Record this amount on the Urine Record Card. Notice the color and smell of the urine and write these on the Record Card, also.

11 Empty the Collection Container. Wash the Container with Antibacterial Soap and water. Rinse it well. Close the cap on the tube of Lubricating Jelly. Put all the supplies back in the box. Throw away the Paper Wash Cloth and take away the Underpad.

12 The Catheter should be dry by this time. Put it inside the Plastic Bag marked "Clean Catheter" and zip it closed.

*The caregiver may take off the gloves now, throw them away and wash their hands.*

When You Travel

A For every four hours you expect to be away, put into the Fanny Pack:
- A clean Catheter in the "Clean Catheter" Bag
- One Packet of Lubricating Jelly
- Two clean paper towels Also put in the pack of pre-wet Travel Wipes and the "Used Catheter" Bag.

B When it is time to do your procedure, find a place like a bathroom and follow Steps 1-12 above, using the paper towels for a clean work surface.

C When you take the Catheter out, rinse it off if possible and store it in the "Used Catheter" Bag. Wash and dry your hands.

D When you are home again, wash your used Catheters very well with Antibacterial Soap and water. Store them in your "Clean Catheter" Bag.

*If you need more supplies, keep the box, this Careguide™ Step-by-Step, the Fanny Pack and your Collection Container. Find the reorder form in the box and call the toll-free number 2 or 3 days before you run out.*

Cateterización Intermitente para el hombre — Paso a Paso

*pagina 1*

*Esta Guía debe ser usada solmente con la orden de su doctor. Esta guía no substituye las instrucciónes de su doctor o enfermera. Todas las provicones necesarias estan en la caja. El nombre de cada objeto está escrito a color. Lea todos los pasos y use el mapa para localizar cada uno antes de empezar. Mantenga todo en la caja hasta que la guía le diga cuando usarlo*

Preparativos

1 Busque una toalla limpia y fresca. Lavese las manos con el Jabón Antibacterial y agua tibia. Sequelas solo con la toalla limpia.

*Si tiene a una persona ayudandolo, el o ella debe de ponerse los Guantes despues de averse lavado las manos.*

Use dos Toallas de papel limpias como superficie para poder trabajar. Si Ud. va a hacer el procedimiento en la cama o en una silla, ponga las Telas para Protejer debajo de su recto.

2 Lave su pene con el Paño para Lavarse, el Jabón Antibacterial, y agua tibia. Limpie la cabeza de su pene muy bien. Si Ud. no ha sido circumcisado, mueva su piel hacia arriba para poder lavarse mejor.

Remoje el Paño para Lavarse, exprimalo hasta que este seco y pongalo en la esquina de una de las toallas de papel. Lave y seque sus manos otra vez.

*Su ayudante usando guantes no tiene que lavarse otra vez.*

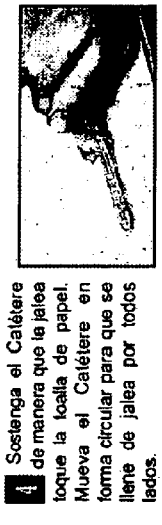

El Catétere

3 Saque el Catétere de su empaquetaje y coloquelo en la toalla de papel. Abra el pomo de Jalea para lubricar. Exprima 3 inches de jalea en el Catétere, empezando por la punta fina. Tenga cuidado de no tocar el Catétere con el pomo de jalea.

4 Sostenga el Catétere de manera que la jalea toque la toalla de papel. Mueva el Catétere en forma circular para que se llene de jalea por todos lados.

5 Recoja el Catétere de la tolla de papel y coloque la punta gruesa del Catétere en el Cofre de Coleccionar Orina. Acerque el cofre a su cuerpo para así evitar que Ud. accidentalmente jale el Catétere fuera del cofre.

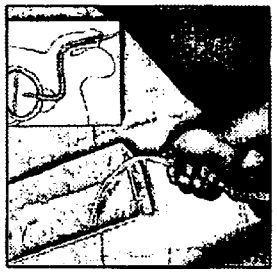

6 Sostenga el pene en posición recta y firmemente con una mano, y meta el Catétere con la otra. Jale el pene hacia fuera de su cuerpo para mantener el canal recto. Empuje el Catétere hacia adentro hasta que orine un poquito. Si el Catétere se detiene, espere un minuto para que se relaje el musculo, y despues trate de meterlo otra vez.

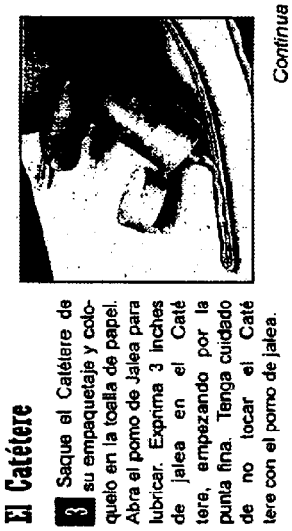

7 Lentamente meta el Catétere otro inche más. Ahora rebaje el angulo de su pene. La bejiga se vaciara mientras Ud. mantenga el Catétere en posición. Cuando deje de orinar, lentamente saque el Catétere.

*Continua atrás...*

SELF CARE DOCUMENTATION — PATIENTS NAME

Male Clean Intermittent Catheterization — *Step-by-Step* — page 1

This sheet is a reduced-size copy of the patient's illustrated, full color instructions. The purpose of this sheet is to confirm that self care training has been carried out by the clinician and understood by the patient and/or caregiver.

This guide is to be followed only on the order of a physician. This guide is not a substitute for your health care professional's instructions.

All the medical supplies you need are in this kit. The name of each item is printed in color below. Read all the steps and use the Map to locate each one before you begin. Keep everything in the box until the guide tells you to use it.

Prepare for Care

1. Get a clean, fresh towel. Wash your hands with Antibacterial Soap and warm water. Dry them only on the fresh towel.

*If you have a caregiver do this procedure for you, they should put on the Gloves after washing their hands.*

Spread out two clean paper towels for a work surface. If you are going to do the procedure on a bed or chair, put the Underpad under your buttocks.

2. Wash your penis with the Paper Wash Cloth and Antibacterial Soap and warm water. Clean the head of your penis well. If you are uncircumcised, pull the foreskin back to wash well.

Rinse the Paper Wash Cloth clean, squeeze it dry and place it on a corner of one of the paper towels. Wash and dry your hands again.

*A caregiver wearing gloves does not need to wash again*

The Catheter

3. Take the Catheter out of the package and lay it on the paper towel. Flip open the cap of the Lubricating Jelly. Squeeze 3 inches of Jelly onto the Catheter, starting at the tip. Be careful not to touch the Catheter with the tube.

4. Hold the Catheter an inch behind the Jelly. Roll it so that the Jelly covers all sides.

5. Lift the Catheter away from the paper towel and lay the wide end in the Collection Container. Move the Container close to your body so you do not accidentally pull the wide end of the Catheter out.

6. Hold the penis straight out with one hand and insert the Catheter with the other hand. Pull the penis away from your body to keep the channel straight. Push the Catheter in until a bit of urine comes out.

*If the Catheter stops, wait a minute to let the muscles relax, then gently begin to push again.*

7. Push the Catheter in another inch, slowly. Now lower the angle of the penis. The bladder will empty while you hold the Catheter in place. When the urine stops, slowly pull the Catheter out.

Patient Name _____
Provider Name _____
Date _____

Check here when Page 1 of training is complete. ☐
Provider initials _____
Patient initials _____

Male Clean Intermittent Catheterization — *continued...* — page 2

Clean for Next Time

8. Take the Catheter to a sink and wash it with Antibacterial Soap and warm water. Hold the Catheter under running tap water to rinse well, inside and out. Shake it several times to get off extra water.

9. Place the Catheter on the clean paper towel to air dry. Pick up the Paper Wash Cloth you left on the paper towel and use it to remove any Jelly left on the head of your penis. Pull the foreskin back down.

10. Check the level of urine in the Container. Record this amount on the Urine Record Card. Notice the color and smell of the urine and write these on the Record Card, also.

11. Empty the Collection Container. Wash the Container with Antibacterial Soap and water. Rinse it well. Close the cap on the tube of Lubricating Jelly. Put all the supplies back in the box. Throw away the Paper Wash Cloth and take away the Underpad.

12. The Catheter should be dry by this time. Put it inside the Plastic Bag marked "Clean Catheter" and zip it closed.

*The caregiver may take off the gloves now, throw them away and wash their hands.*

When You Travel

A. For every four hours you expect to be away, put into the Fanny Pack:
- A clean Catheter in the "Clean Catheter" Bag
- One Packet of Lubricating Jelly
- Two clean paper towels Also put in the pack of pre-wet Travel Wipes and the "Used Catheter" Bag.

B. When it is time to do your procedure, find a place like a bathroom and follow Steps 1-12 above, using the paper towels for a clean work surface.

C. When you take the Catheter out, rinse it off if possible and store it in the "Used Catheter" Bag. Wash and dry your hands.

D. When you are home again, wash your used Catheters very well with Antibacterial Soap and water. Store them in your "Clean Catheter" Bag.

*If you need more supplies, keep the box, this Careguide™ Step-by-Step, the Fanny Pack and your Collection Container. Find the reorder form in the box and call the toll-free number 2 or 3 days before you run out.*

Check here when Page 2 of training is complete. ☐
Provider initials _____
Patient initials _____

We agree that the patient understands these instructions and is ready to carry out self care:

_____ Provider Signature
_____ Patient Signature

FIG. 5

URINE RECORD GUIDE

Patient Name: [        ]

*Your doctor will tell you how often to record your urine output. Remember to circle AM or PM when you write the time.*

| Date | Time | Quantity | Time | Quantity | Time | Quantity | Time | Quantity | Time | Quantity | TOTAL | Comments |
|---|---|---|---|---|---|---|---|---|---|---|---|---|
|  | AM PM |  | AM PM |  | AM PM |  | AM PM |  | AM PM |  |  |  |
|  | AM PM |  | AM PM |  | AM PM |  | AM PM |  | AM PM |  |  |  |
|  | AM PM |  | AM PM |  | AM PM |  | AM PM |  | AM PM |  |  |  |
|  | AM PM |  | AM PM |  | AM PM |  | AM PM |  | AM PM |  |  |  |
|  | AM PM |  | AM PM |  | AM PM |  | AM PM |  | AM PM |  |  |  |
|  | AM PM |  | AM PM |  | AM PM |  | AM PM |  | AM PM |  |  |  |
|  | AM PM |  | AM PM |  | AM PM |  | AM PM |  | AM PM |  |  |  |
|  | AM PM |  | AM PM |  | AM PM |  | AM PM |  | AM PM |  |  |  |
|  | AM PM |  | AM PM |  | AM PM |  | AM PM |  | AM PM |  |  |  |
|  | AM PM |  | AM PM |  | AM PM |  | AM PM |  | AM PM |  |  |  |
|  | AM PM |  | AM PM |  | AM PM |  | AM PM |  | AM PM |  |  |  |
|  | AM PM |  | AM PM |  | AM PM |  | AM PM |  | AM PM |  |  |  |
|  | AM PM |  | AM PM |  | AM PM |  | AM PM |  | AM PM |  |  |  |
|  | AM PM |  | AM PM |  | AM PM |  | AM PM |  | AM PM |  |  |  |

Catherize yourself ____ times a day at ____. Each day drink ____ 8oz. glasses fluid, but no more than ____ 8oz. glasses fluid. Your medication is: ____

MALE CLEAN INTERMITTENT CATHETER SYSTEM

PRIORITY CLAIM

This application claims the benefit of provisional application Serial No. 60/211,152, filed Jun. 13, 2000.

CROSS-REFERENCE TO RELATED APPLICATIONS

This application is related to the following commonly-owned patent applications: "A PATIENT DISCHARGE SYSTEM AND METHOD FOR POST BREAST SURGERY CARE," Ser. No. 09/640,680, abandoned; "METHOD FOR DETERMINING THE CONTENT OF A SELF-CARE KIT," Ser. No. 09/709,917; "PATIENT DISCHARGE SYSTEM AND METHOD FOR SELF-CARE OF A POST-SURGERY DRAIN," Ser. No. 09/779,796; "ANTIBIOTIC DRESSING CHANGE SYSTEM," Ser. No. 09/808,535, abandoned; "NORMAL SALINE DRESSING CHANGE SYSTEM," Ser. No. 09/808,323, abandoned; "CIRCUMCISION AFTERCARE SYSTEM," Ser. No. 09/808,335; "FEMALE CLEAN INTERMITTENT CATHETER SYSTEM," Ser. No. 09/879,230; and "A PATIENT DISCHARGE SYSTEM AND METHOD FOR POST CARDIAC SURGERY CARE" Ser. No.09/878,671.

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

1. Description

The present invention relates in general to a system and method for using a male catheter and in particular to a system and method for clean intermittent male catheterization by a user or health care provider.

2. Background of the Invention

It is estimated that urinary catheters are placed in millions of men each year in the United States alone, either due to some illness, infection or malfunction or as part of some medical procedure. Care must be taken to clean the catheter site to reduce the risk of nosocomial infection (i.e., an infection that arises due to a procedure for treating a disorder and unrelated to the disorder itself, also referred to as a "hospital infection").

The most common nosocomial infections are related to or arise from indwelling urinary bladder catheters (i.e., catheters that remain in the urinary tract for a relatively long length of time). The risk of such catheter-related nosocomial infections can be reduced using strict aseptic techniques (i.e., using gloves, disinfectants, antibacterial soaps, etc.) when handling the catheter. Moreover, the risk of infection can further be reduced by only using a catheter intermittently rather leaving the catheter in place for any length of time. Intermittent use of the catheter in conjunction with clean techniques helps to reduce the risk of catheter-related nosocomial infections and is, moreover, a far more attractive alternative for bladder evacuation to most patients who are candidates for the procedure.

Using a urinary bladder catheter under aseptic conditions in a hospital is routine. However, current medical practice emphasizes getting the patient ambulatory (and out of the hospital) as soon as possible. Consequently, catheterizations or catheter insertions are performed at home by nonprofessionals. These nonprofessionals must be taught clean techniques. However, no known comprehensive devices, apparatus or methods exists for teaching clean techniques or for facilitating such home catheter use for men.

SUMMARY OF INVENTION

The present invention provides a method and system for intermittent catheterization by the patient himself, the patient's caregiver, or a health care provider. The present invention contains apparatus for facilitating at least one catheterization and comprises: (I) at least one male catheter; (II) antibacterial soap; (III) lubricant; (IV) step-by step instructions; and (V) a container, where the above named items are positioned inside the container. It should be appreciated that the present invention may only be used on the order of a physician.

Preferred embodiments of the system contain sufficient apparatus for one month of catheter insertions (approximately 3 to 4 times a day), the antibacterial soap is in liquid form, the lubricant is in gel form, the step-by-step instructions are written in English and Spanish, although other languages (e.g., Polish, French and German for example) are contemplated. One preferred embodiment of the system includes a contents map identifying the contents and the positions of the contents, along with zipper bags, a fanny pack and a protective underpad.

In a more preferred embodiment of the system, the system contains apparatus for at least one month of catheterizations as provided previously and comprises: (I) 4 male intermittent catheters; (II) 35 disposable wipes; (III) 1 protective underpad; (IV) antibacterial liquid soap; (V) 1 tube of lubricant; (VI) step-by-step instructions; (VII) clinician step-by-step instructions or self-care documentation; and (VIII) a box, wherein the above-named items are positioned inside the box.

The method for intermittent male catheterization comprises evacuating the bladder using the apparatus of the present invention in accordance with the detailed step-by-step instructions provided in the system. In a preferred embodiment, the method which is discussed in further detail below generally includes: (I) preparing for intermittent male catheterization; (II) preparing the male catheter; (III) inserting the male catheter; (IV) draining the bladder; (V) recording and disposing of the drainage; and (VI) cleaning and storing the apparatus of the present invention.

The present invention further includes a patient education system for educating users in performing intermittent male catheterization. Specifically, the system includes a system and a set of black and white step-by-step instructions without illustrations (referred to herein as self-care documentation). An instructor (i.e., a doctor, nurse, clinician or other medical professional) uses the self-care documentation to educate the user in performing an intermittent male catheterization, preferably using the system of the present invention. The medical professional then keeps the self-care documentation documenting that the user was educated in performing the male catheterization.

It is therefore an object of the present invention to provide a system and method for intermittent male catheterization.

It is a further object of the present invention to provide detailed instructions for intermittent male catheterization using the contents of a self-care system.

An additional object of the present invention is to provide self-care documentation to be used by a medical professional in instructing users in the use of the self-care system.

Yet an additional object of the present invention is to provide a patient education system for educating users in performing intermittent male catheterization using the system.

Other objects, features and advantages of the invention will become apparent from the following detailed disclosure, taken in conjunction with the accompanying sheets of drawings, wherein like numerals refer to like parts, components and processes.

BRIEF DESCRIPTION OF THE DRAWINGS

FIGS. 2A and 2B are top plan views of the step-by-step instructions in English of the system of the present invention;

FIGS. 3A and 3B are top plan views of the step-by-step instructions in Spanish of the system of the present invention;

FIG. 4 is a top plan view of the self-care documentation in English used by a medical professional for documenting that the users are instructed in the use of the system of the present invention; and FIG. 5 is a top plan view of the urine record card.

DETAILED DESCRIPTION OF THE INVENTION

It should be appreciated that the figures include one or more of the following trademarks which may be used by the assignee of this application: (a) CAREGUIDE; and (b) CAREGUIDE and DESIGN. It should be appreciated that these trademarks are not part of the present invention.

The present invention is for a system 10 and method for intermittent catheterization of a patient. The user may be the patient himself, the patient's caregiver, an in-home care provider or a healthcare provider which, for brevity, are referred to herein as the "user." The system 10 provides apparatus needed for in-home catheterization.

In general, the intermittent catheterization system 10 contains at least: (I) infection prevention devices (gloves, disposable wipes, zipper bags, alcohol gel (i.e., a waterless cleaner), soap, and protective underpads); (II) insertion devices (catheter and lubricant); (III) recording devices (urine record card and collection basin); and (IV) information devices (step-by-step instructions, contents map and self-care documentation) among other items.

Figure 1:
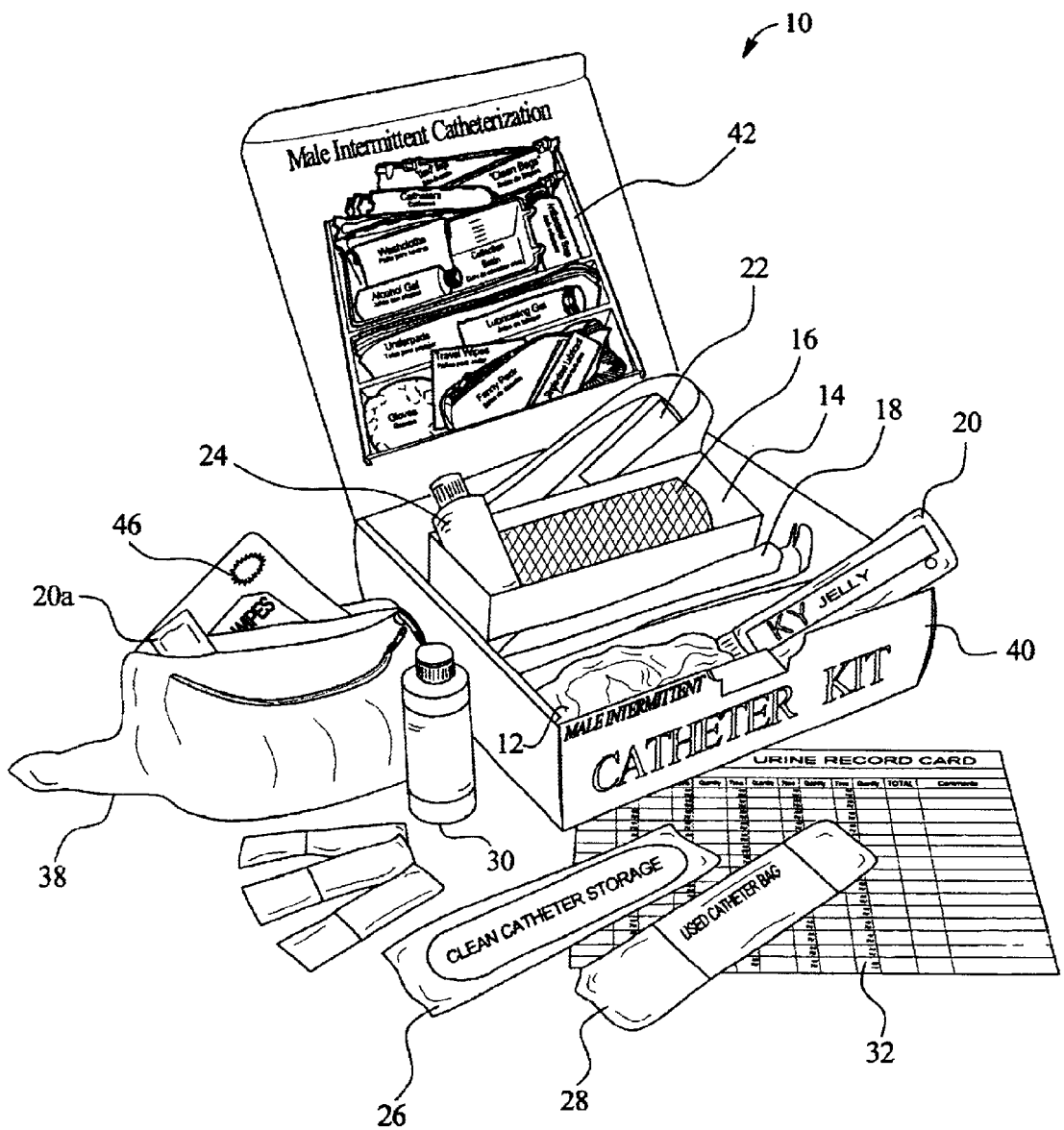
FIG. 1 is a perspective view of the system of the present invention.
Figure 1A:
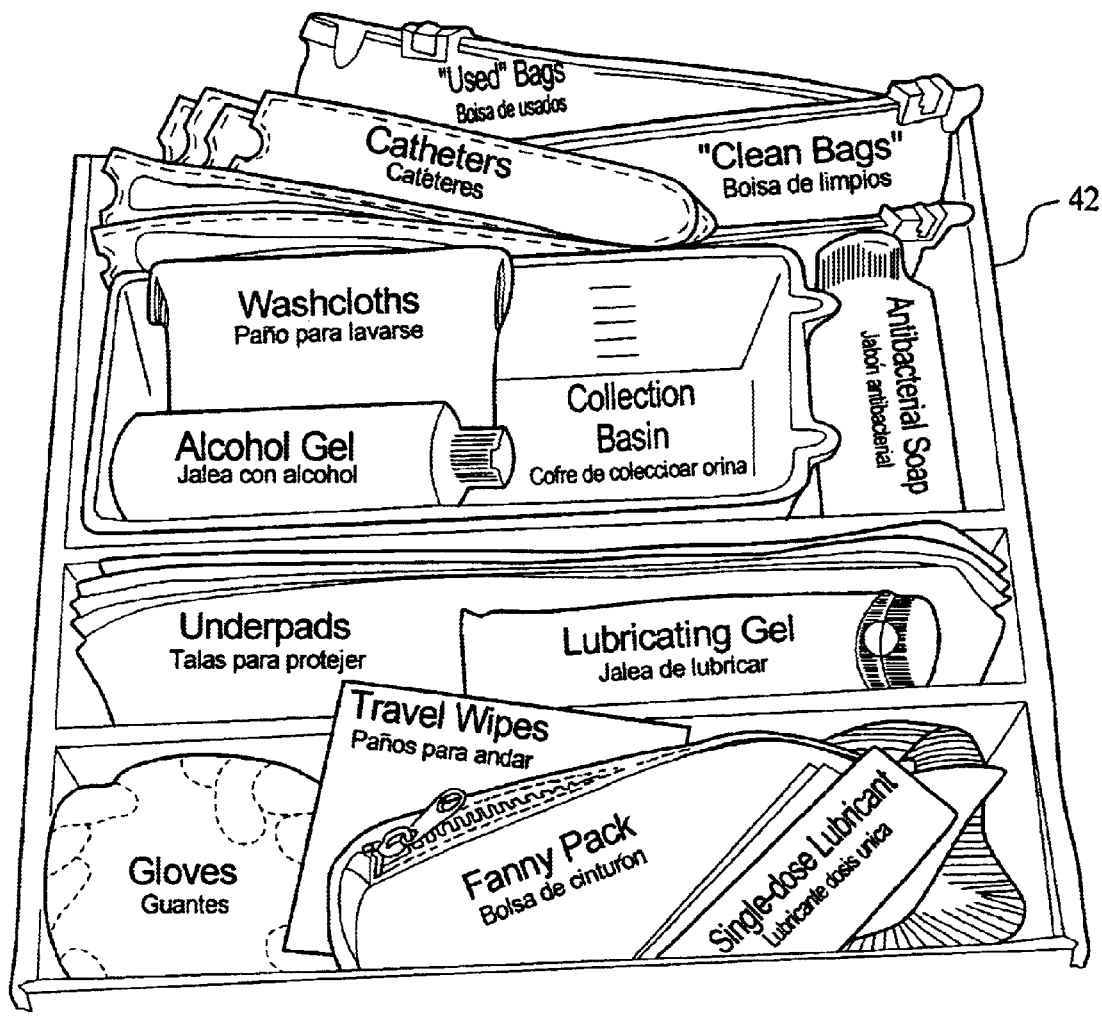
FIG. 1A is a top plan view of a contents map of the present invention.

More specifically, as illustrated by FIGS. 1 and 1A, the intermittent catheterization system 10 of the present invention comprises: (I) gloves 12; (II) a collection basin 14; (III) disposable wipes 16; (IV) protective underpad 18; (V) antibacterial soap 24; (VI) lubricating gel 20; (VII) male intermittent catheter 22; (VIII) clean and used zipper bags 26 and 28 respectively; (IX) self-care documentation 44 (not shown in FIGS. 1 and 1A); (X) step-by-step instructions 34 (not shown in FIGS. 1 and 1A); and (XI) a container or box 40. It is contemplated that the system 10 may also include a contents map 42 which identifies the contents of the container 40 and their position, and one or more waste bags.

In one preferred embodiment, the container 40 contains gloves 12, a plastic collection basin 14 with graduated markings, disposable wipes 16, protective underpads 18, single doses of lubricating gel 20a, male 14 catheters 22, antibacterial liquid soap 24, clean catheter zipper bags 26, a used catheter zipper bag 28, alcohol gel 30, a urine record card 32, a lubricating gel tube 20, a fanny pack 38, a travel wipe pack 46, illustrated step-by-step instructions documentation 34 as revealed by FIGS. 2A and 2B, and 3A and 3B, and self-care documentation 44). It should be appreciated that system 10 could be provided to the patient in a box, tray, bag, container or any other suitable content holder device 40. A box is preferred because it is strong enough to protect the contents of the system 10 and yet is suitable for shipping and storing. If a bag, tray, container or other content holding devices are used, a contents map 42 may or may not be included with system 10.

Figure 3B:
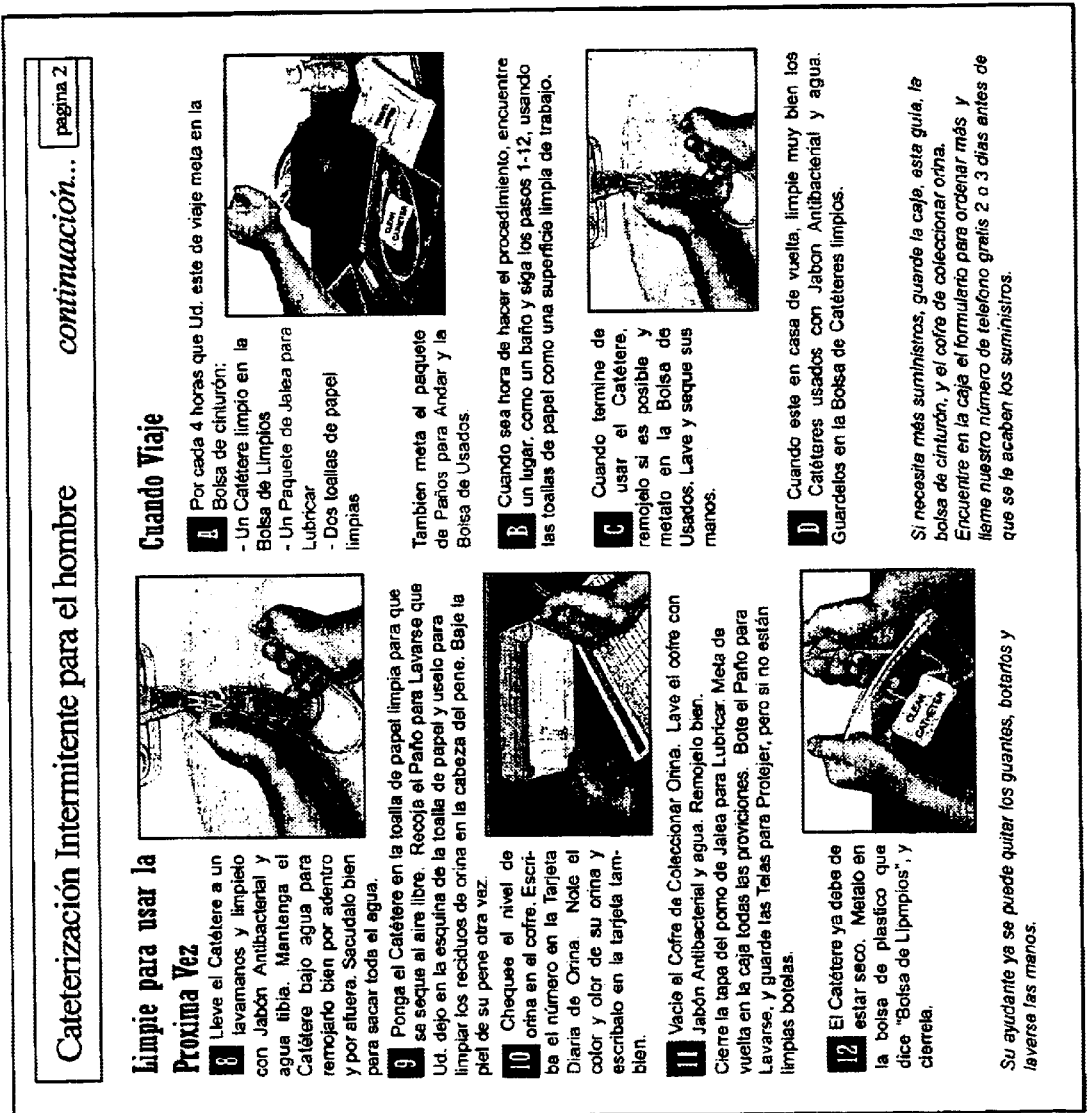

In one preferred embodiment, a urologist, clinician or other medical professional provides system 10 to the user, although it is contemplated that the user could obtain system 10 through other means provided that a medical professional has ordered the system for the patient. System 10 includes extremely detailed and specific step-by-step instructions 34 as illustrated in FIGS. 2A and 2B that the user uses with the intermittent catheterization system 10 (specific step-by-step instructions in Spanish are illustrated in FIGS. 3A and 3B). System 10 also includes the self-care documentation 44 the medical professional uses to document or record the instructions provided to the user in the use of the intermittent male catheterization system 10 as illustrated in FIG. 4. A difference between the two sets of instructions is that the instructions in FIG. 4 are black and white and include acknowledgment sections 45A and 45B while the instructions in FIGS. 2A and 2B are illustrated in color (not shown) for ease of use by the patient. It is also contemplated that system 10 could include an instructional video, training the user in the use of the system 10.

In one preferred embodiment, system 10 includes sufficient apparatus for one month of male catheter insertions, the antibacterial soap 24 is in a liquid form, the lubricant 20 is provided in a gel or ointment form, and the step-by-step instructions 34, and the contents map 42 (if included) are written in English. While not necessary, one preferred embodiment also includes one or more gloves 12, disposable wipes 16 and a protective underpad 18. It should be appreciated that a user could order a refill of the disposable apparatus of the present invention using an order form provided with the apparatus of the present invention.

In a more preferred embodiment of the system, system 10 includes apparatus for at least one month of catheterizations and comprises: (I) 10 gloves 12; (II) 1 collection basin 14; (III) 35 disposable wipes 16; (IV) 3 protective underpads 18; (V) 10 single tubes of lubricating gel 20; (VI) 4 male intermittent catheters 22; (VII) antibacterial liquid soap 24; (VIII) 4 clean catheter zipper bags 26; (IX) 1 used catheter zipper bag 28; (X) 4 oz of alcohol gel 30; (XI) 1 urine record card 32; (XII) 1 lubricating gel tube 20; (XIII) a fanny pack 38; (XIV) 1 pack of travel wipes 46; (XV) self-care documentation 44; (XVI) detailed step-by-step instructions 34; (XVII) a contents map 42; and (XVIII) container or box 40 wherein the above-named items are positioned inside the box 40.

The system 10 includes apparatus necessary for intermittent male catheterization in accordance with the method. The system 10 organizes the apparatus in an easy-to-find format. The step-by-step instructions 34 indicate when an item is first required during the method and should be removed from the container 40 (preferably using red text to indicate when an item is first required). Using the step-by-step instructions 34 and the contents map 42, users can easily identify when each item is required in the method and readily find it in the container 40. It should be appreciated that the items and step-by-step instructions 34 could be color coded and/or use icons making identifying each item even easier. For example, the antibacterial soap 24 could be identified by a bubbles icon and blue coloring corresponding to a bubbles icon and blue color in the step-by-step instructions 34.

The method of the present invention generally comprises using the system 10 in accordance with the detailed step-by step instructions 34. In a preferred embodiment, the method generally includes: (I) preparing for intermittent male catheterization; (II) preparing the male catheter; (III) inserting the male catheter; (IV) draining the bladder; (V) recording and disposing of the drainage; and (VI) removing the male catheter and cleaning and storing the apparatus.

Preparing for Intermittent Male Catheterization (Step I)

The first step of the method of the present invention, is illustrated by FIGS. 2A and 2B and includes preparing and caring for the male catheterization site. Preparing and caring for the catheterization site includes: (I) obtaining a clean, fresh towel; (II) washing using the antibacterial liquid soap 24 and warm water, and using the clean towel for drying; (III) finding a safe, flat, uncluttered, solid surface; (IV) putting on the gloves 12 only if the catheterization is being performed by a user other than the patient which includes: (a) taking a pair of gloves 12 out of the box 40; and (b) putting them on; (V) preparing the surface which includes: (a) obtaining two clean, fresh paper towels; (b) opening the two paper towels; (c) placing the opened paper towels on the surface; (d) taking a protective underpad 18 out of the box 40; (e) opening the protective underpad 18; and (f) placing the opened protective underpad 18 under the patient's buttocks and near the opened paper towels; (VI) cleaning the catheter site which includes: (a) taking a paper wash cloth or disposable wipe 16 out of the box 40; (b) taking the container of antibacterial soap 24; (c) squeezing out approximately one or two drops of soap 24 onto the center of the wipe 16; and (d) gently washing the site using the wipe 16, the soap 24 and warm water; (VII) rinsing clean the wipe 16 which includes: (a) rinsing the wipe 16; (b) squeezing out the excess water, leaving the wipe 16 damp; and (c) placing the damp wipe 16 on one corner of the paper towel; and (VIII) washing using the antibacterial soap 24 as described previously. It should be appreciated that step (VII) can be skipped if the user is wearing gloves 12. It is also contemplated that step I could include: (IX) preparing a waste bag comprising: (a) obtaining a waste bag; (b) opening the waste bag; and (c) setting the waste bag on the flat surface.

Preparing the Male Catheter (Step II)

The second step of the method as illustrated includes inserting the catheter 22 into the penis. Inserting the catheter 22 includes: (I) taking a catheter 22 out of the box 40; (II) laying the catheter 22 on the paper towels; (III) take a collection basin 14 out of the box 40 and placing it near the paper towels; (IV) applying the lubricating gel 20 which includes: (a) taking the lubricating gel tube 20 out the box 40; (b) flipping open the cap of the lubricating gel tube 20; (c) squeezing 3 inches of lubricating gel 20 onto the catheter 22 starting at the tip, being careful not to touch the catheter 22 with the tube 20; (d) rolling the catheter 22 in the lubricating gel 20 so that all sides are covered; (e) lifting the catheter 22 away from the paper towel and laying the wide end of the catheter 22 in the collection basin 14; and (f) moving the basin 14 close to the user so that the wide end of the catheter 22 is not accidentally pulled out of the basin 14.

Inserting the Male Catheter (Step III)

The third step of the present invention comprises inserting the catheter 22 into the penis. Inserting the catheter 22 comprises: (I) sitting on the underpad 18; (II) holding the penis straight out with one hand; (III) pulling the penis away from the body keeping the urinary tract straight; (IV) inserting the catheter 22 until a bit (i.e., at least a drop) of urine appears; and (V) slowly pushing the catheter 22 in one inch more.

Draining the Bladder (Step IV)

The fourth step of the method comprises draining the site (i.e., the bladder) forming a drainage. Draining the bladder using the catheter 22 comprises: (I) placing or holding the basin 14 in proximity to the tip of the catheter 22; (II) lowering the angle of the penis; (III) holding the catheter 22 in place and emptying the bladder into the basin 14; and (IV) slowly pulling the catheter 22 out when the bladder is empty (i.e., the urine stops).

Recording and Disposing of the Drainage (Step V)

The next step of the method includes recording and disposing of the drainage. This step includes: (I) recording the amount of the drainage, including: (a) measuring the drainage level using the markings on the basin 14; (b) writing this amount on the urine record card 32 illustrated in FIG. 5; (c) noticing the color and smell of the drainage; and (d) recording the color and smell on the urine record card 32; and (II) disposing of the drainage, preferably emptying the basin 32 in a toilet.

Cleaning and Storing the Apparatus (Step VI)

The next step includes completing the intermittent catheterization in accordance with the method. Completing the catheterization includes: (I) cleaning the used catheter, which includes: (a) washing the used catheter 22 with the antibacterial soap 24 and warm water; (b) holding the catheter 22 under running tap water, rinsing it well inside and out; (c) shaking the catheter 22 several times to remove any excess water; and (d) placing the catheter 22 on a clean, fresh paper towel to air dry; (II) removing any jelly left on the catheterization site using the damp wipe 16 (See Step I above); (III) cleaning the basin 14, which includes: (a) washing the basin 14 using antibacterial soap 24 and warm water; (b) rinsing the basin with warm water; and (c) placing the basin 14 on clean, fresh paper towel to air dry; (IV) closing the cap on the lubricating gel tube 20; (V) placing all the apparatus back in the box 40; (VI) placing the dry catheter 22 inside a clean catheter zipper bag 26, zipping it closed; (VII) placing the clean catheter zipper bag 26 in the box 40; (VIII) placing the dry basin 14 in the box 40; (IX) placing the underpad 18 in the box 40; and (X) disposing of the wipe 16 and the paper towels, preferably using the waste bags.

It should be anticipated that the patient is not bed bound, but able and willing to get around. One preferred embodiment of the present invention includes a fanny pack 38 that enables users to travel. As illustrated in FIGS. 2A and 2B, method provides that, for every four hours of travel, the fanny pack 38 should include: (I) one clean catheter 22 in a clean catheter zipper bag 26; (II) one packet of lubricating gel 20a; and (III) two clean paper towels. The fanny pack 38 should also include the pack of pre-wet travel wipes 46 and the used catheter zipper bag 28.

When catheterization is required, the user should find a place (preferably a bathroom) and follow Steps I–VI above, using clean paper towels for a clean work surface. After removing the catheter 22 in Step V, rinse it off if possible and store it in the used catheter zipper bag 28, placing the bag 28 in the fanny pack 38. Wash as described previously in Step I. The used catheters may be cleaned completely upon returning home.

The present invention includes teaching or instructing users in the use of system 10. System 10 includes a set of extremely detailed instructions 34 and self-care documentation 44, as illustrated in FIG. 4. The self-care documentation is used by the medical care professional to instruct the users and for medical records.

Federal, state and local regulatory agencies require that the medical professional maintain complete records, including records to training provided to individuals. The medical care professional uses the self-care documentation 44 providing the instruction to the patient or user on the use the method and system 10 as illustrated in FIG. 4. The self care documentation enables the medical care professional to ensure that the training is complete, providing a signature box or acknowledgment areas 45A and 45B for the user to indicate that they received and understand the instructions. This documentation 44 is maintained by the clinician or a medical provider as part of the clinical record, where they may be used for accreditation and/or legal purposes.

The present invention further contemplates a patient education system for educating users in performing intermittent male catheterization. The system includes the system 10 and the self-care documentation 44. The present invention is only used on the order of a physician. An instructor (i.e., a doctor, nurse, clinician, other medical profession, or any individual trained to educate users in performing male catheterization) uses the self-care documentation 44 to train users to perform a male catheterization, preferably using the system 10. The instructor takes the user through the process of performing a male catheterization, and may even demonstrate specific procedures using specific items in the system 10. For example, it is contemplated that the instructor could demonstrate how to apply lubricating gel to the catheter 22, clean the catheter 22, record drainage, etc. It should be appreciated that the instructor could use a model to demonstrate how to insert the catheter 22, drain the bladder and remove the catheter 22.

It should be appreciated that the system 10 may contain sufficient apparatus for one or more catheter insertions; for example, apparatus for two, three, four or more months of catheter usage are contemplated. Further, it should be appreciated that refills for system 10 may be provided. In a preferred embodiment, a reorder form may be provided in system 10.

While the present invention has been described in connection with what is presently considered to be the most practical and preferred embodiments, it is to be understood that the invention is not limited to the disclosed embodiments, but on the contrary is intended to cover various modifications and equivalent arrangements included within the spirit and scope of the claims. It is thus to be understood that modifications and variations in the present invention may be made without departing from the novel aspects of this invention as defined in the claims, and that this application is to be limited only by the scope of the claims.

The invention is hereby claimed as follows:

1. A patient education system for educating a user in performing intermittent male catheterization, said system comprising:
   a male catheterization system including at least one male catheter;
   (a) ten gloves;
   (b) a collection basin;
   (c) thirty five disposable wipes
   (d) three protective underpads;
   (e) four male catheters;
   (f) ten single doses of lubricant gel;
   (g) antibacterial liquid soap;
   (h) four clean catheter zipper bags;
   (i) a used catheter zipper bag;
   (j) a container of alcohol gel;
   (k) a urine record card;
   (l) a lubricating gel tube;
   (m) a fanny pack;
   (n) step-by-step instructions;
   (o) a box wherein items (a) through (n) are positioned inside the box; and
   self-care documentation an instructor uses to educate the user in performing intermittent male catheterization using the system.

2. A system for intermittent male catheterization used by a user and containing apparatus for at least one catheter insertion, said system comprising:
   (a) at least one male catheter;
   (b) antibacterial soap;
   (c) lubricant;
   (d) at least one set of step-by-step instructions; and
   (e) at least one container for holding the system.

3. The system of claim 2, which includes self-care documentation including an acknowledgement section for documenting instructions provided to the user in the use of the system.

4. A method for intermittent catheterization by a user comprising inserting a catheter with the system of claim 2.

5. A system for intermittent male catheterization used by a user and containing apparatus for a plurality of male catheter insertions, said system comprising:
   (a) ten gloves;
   (b) a collection basin;
   (c) thirty disposable wipes
   (d) three protective underpads;
   (e) four male catheters;
   (f) ten single doses of lubricant gel;
   (g) antibacterial liquid soap;
   (h) four clean catheter zipper bags;
   (i) a used catheter zipper bag;
   (j) a container of alcohol gel;
   (k) a urine record card;
   (l) a lubricating gel tube;
   (m) a set of step-by-step instructions; and
   (n) a box wherein items (a) through (m) are positioned inside the box.

6. The system of claim 5, which includes self-care documentation for documenting instructions provided to the user in the use of the system.

* * * * *